United States Patent [19]
Carbo et al.

[11] Patent Number: 5,250,060
[45] Date of Patent: Oct. 5, 1993

[54] ANGIOPLASTY APPARATUS

[76] Inventors: Paul L. Carbo, 91 Village St., Northford, Conn. 06472; John F. Setaro, 87 Kent Ct., Meriden, Conn. 06450

[21] Appl. No.: 904,552

[22] Filed: Jun. 26, 1992

[51] Int. Cl.$^5$ ............................................. A61B 17/32
[52] U.S. Cl. ................................ 606/159; 606/170; 606/194; 604/22; 604/96
[58] Field of Search ............... 606/159, 170, 171, 180, 606/191, 194; 128/750-757; 604/22, 96-101

[56] References Cited

U.S. PATENT DOCUMENTS

| | | | |
|---|---|---|---|
| 4,631,052 | 12/1986 | Kensey | 606/159 |
| 4,784,636 | 11/1988 | Rydell | 606/159 |
| 4,926,858 | 5/1990 | Giffuro, III et al. | 606/170 |
| 4,950,238 | 8/1990 | Sullivan | 604/22 |
| 4,957,482 | 9/1990 | Shiber | 606/159 |
| 5,074,841 | 12/1991 | Ademovic et al. | 606/159 |
| 5,135,531 | 8/1992 | Shiber | 604/22 |

FOREIGN PATENT DOCUMENTS

| | | | |
|---|---|---|---|
| 0229620 | 7/1987 | European Pat. Off. | 606/159 |
| 3519626 | 12/1986 | Fed. Rep. of Germany | 606/159 |

*Primary Examiner*—C. Fred Rosenbaum
*Assistant Examiner*—William Lewis
*Attorney, Agent, or Firm*—Edward R. Hyde

[57] ABSTRACT

An angioplasty apparatus for removing abnormal deposits such as atheromatic plaque from the internal arterial walls is provided. The apparatus includes an elongated, flexible mechanism for insertion in an artery to the location of plaque deposit. Two inflatable occluder balloons are provided to be positioned at either ends of the plaque section and inflated to seal off the section. A milling balloon is adapted to be positioned in the plaque section to be rotated and bear against an expandable milling surface which is gradually expanded as the plaque deposit is milled away. Because of the sealing balloons, the plaque particles are prevented from passing into the arterial stream and may be taken away through a tubular channel.

9 Claims, 4 Drawing Sheets

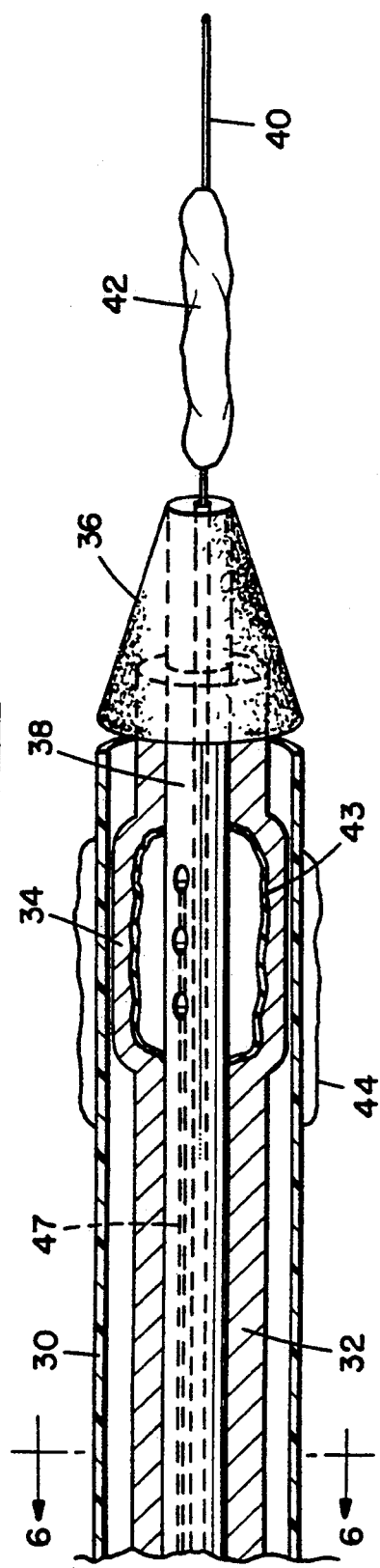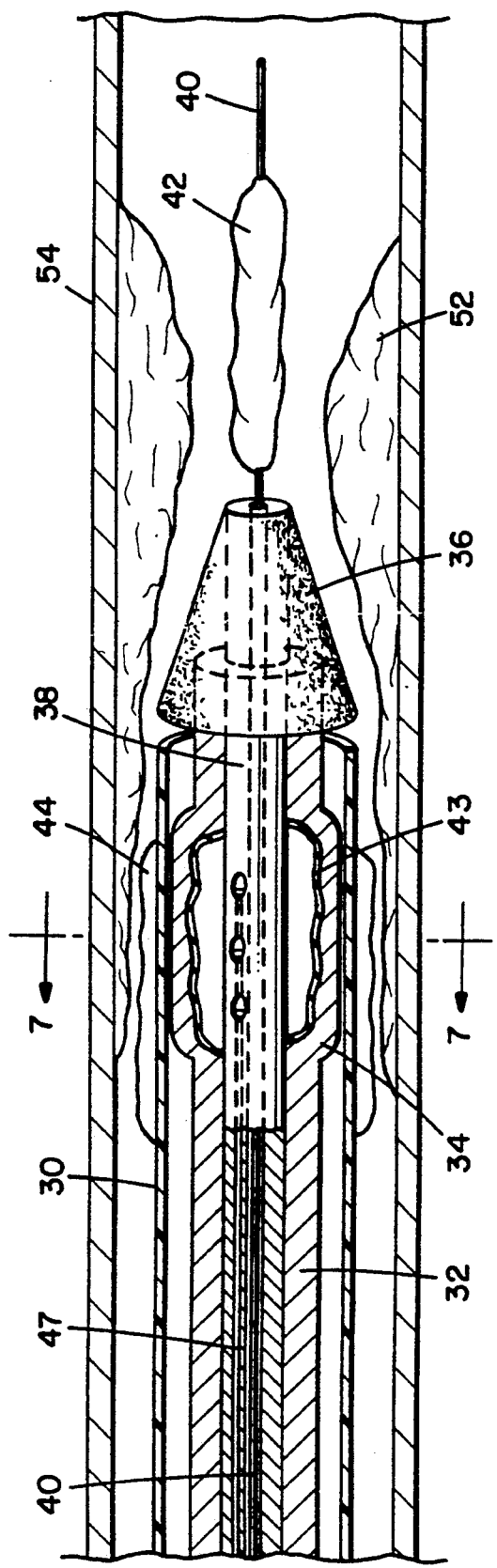

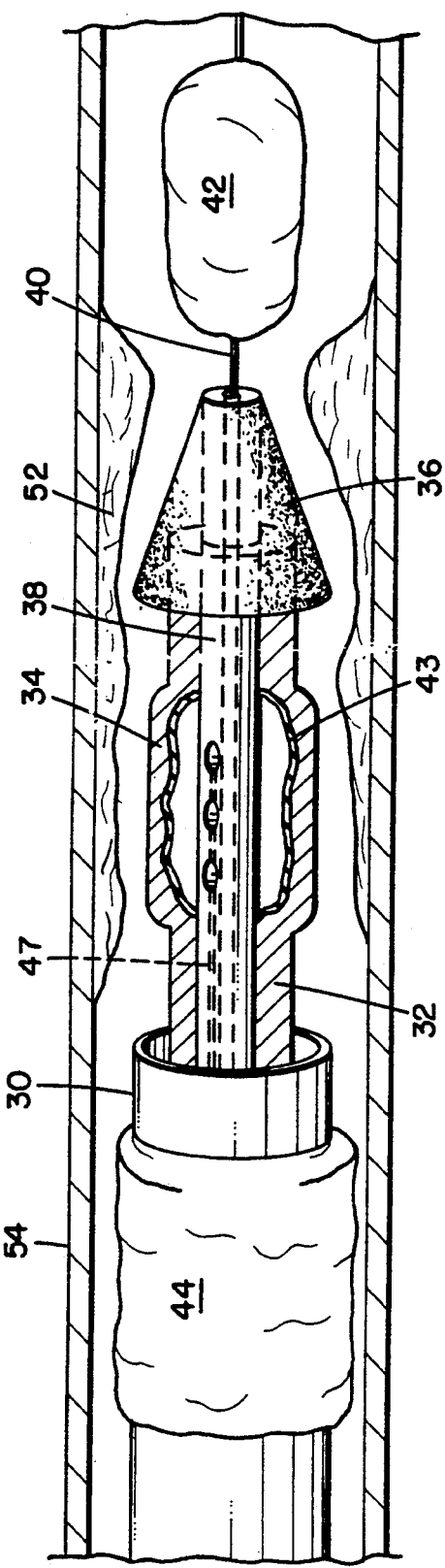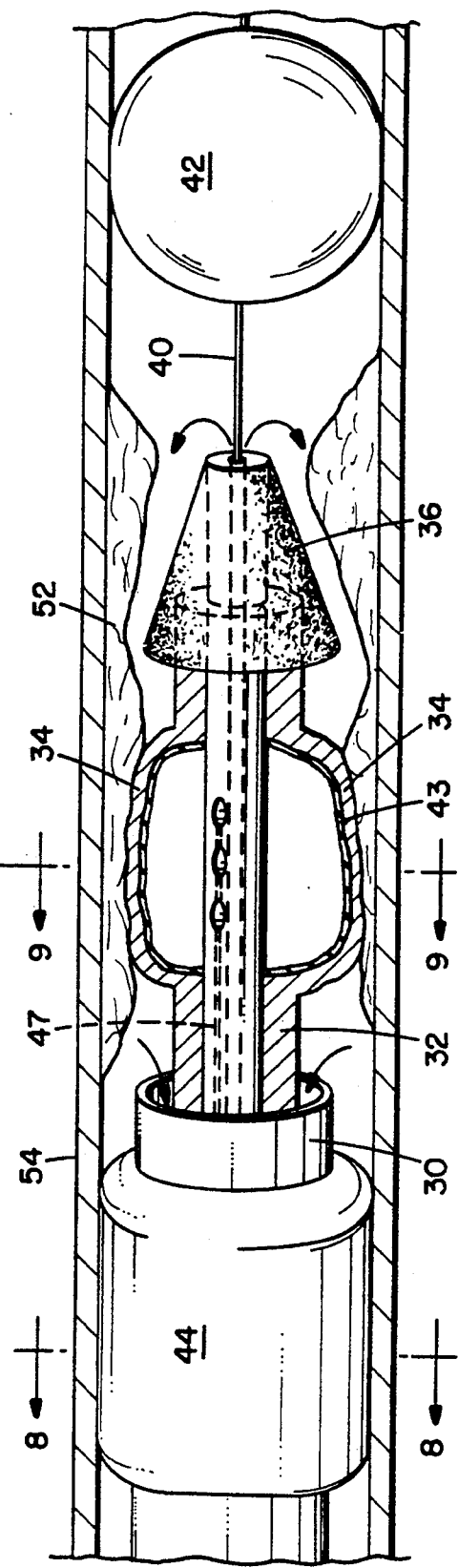

ANGIOPLASTY APPARATUS

BACKGROUND OF THE INVENTION

This invention relates to the field of noninvasive surgery for the relief of atherosclerotic obstructions of arteries known as angioplasty or the internal remodeling of arteries in which there is physical displacement of the atherosclerotic material. Such noninvasive surgery comprises methods of repair of diseased or distorted internal bodily structures through the use of instruments placed via skin puncture rather than a large operative incision.

The invention contemplates a catheter adapted to be inserted in the blood vessel that may have a section of abnormal deposits such as atherosclerotic plaque, for the purpose of cutting away the deposits.

A number of current methods for removing such deposits exists that are designed to treat this problem of vessel obstruction. However significant problems and limitations apply to the prior art approaches.

A widely employed approach is percutaneous transluminal balloon angioplasty in which a large bore guiding catheter is placed in a peripheral artery and through this guiding catheter a balloon catheter is passed to the section of the artery to be treated and the balloon is inflated within the arterial narrowing or lesion. The purpose of this procedure is to disrupt or push aside atherosclerotic plaque material that is obstructing the vessel so that blood flow to the region fed by that vessel is improved. Disadvantages of the method include acute vessel closure or collapse requiring emergency coronary artery bypass surgery and also reappearance of the blockage. The procedure may also be accompanied by thrombus formation and dissection. Means for alleviating particularly long blockages have not been successful and also means of administering drug therapy directly to the affected site is limited. Refinements and modifications of this technique include atherectomy devices through which atherscolorotic material is removed by shaving or milling and also the use of laser energy. In general the uses of these devices which are often more complex and expensive than conventional balloon catheters and often require adjunctive balloon catheter dilation has not improved the overall rate of restenosis. In addition the issues of how to avoid damage to normal healthy arterial wall and how to protect and remove detached atherosclerotic debris have required further attention.

An example of the prior art apparatus is shown in U.S. Pat. No. 4,445,509 to Auth which shows apparatus for the removal of deposits by means of a cutting tool secured at one end of a flexible rotating shaft adapted to be inserted into a blood vessel. An actuator rotates the cutting tool to remove the deposits from the vessel walls and thereafter the particles of deposit are dispersed in the bloodstream without actually being removed from the body.

In this type of apparatus the rotating tool is of fixed diameter and mills and opening in the occluded or plaque deposit section in accordance with the tool diameter. To open a section that is heavily deposited it is often necessary to use a first cutting tool of small diameter and then subsequent tools of progressively larger diameters.

This need for multiple tools of different diameters to open an occluded section is a particular disadvantage of such prior art devices.

A further disadvantage of devices of the prior art is that particles of plaque deposit pass into the blood stream after they are milled by the cutting tool.

SUMMARY OF THE INVENTION

Against the foregoing background it is a primary object of the present invention to provide an angioplastic device and method for removing abnormal plaque deposits from arterial walls in an efficient and safe manner.

A further object of the present invention is to provide an angioplastic device of the rotating cutter type in which the cutter is radially expandable.

A still further object of the present invention is to provide an expandable cutter for an angioplastic device to permit a small opening in an occluded blood vessel section to be gradually expanded in diameter without changing cutting tools.

It is a further object of the present invention to provide a device for removing plaque deposits from vessel walls in which the particles are prevented from passing into the blood stream of the patient.

Another object of the present invention is to provide an angioplastic device in which the abnormal deposits from the blood vessel walls are cut away and conveniently and thoroughly withdrawn from the blood vessel.

A still further object of the present invention is to provide an angioplastic device in which the section of blood vessel having abnormal plaque deposits is temporarily sealed off from the remaining portions of the vessel during the period in which the deposit is cut away or milled so that particles cannot pass into the blood stream.

The device of the present invention comprises an elongated catheter mechanism adapted to be inserted into a blood vessel to the location of plaque deposit that is required to be removed. The catheter includes a plurality of concentric elongated members that provide channels for fluid pressures to be applied to inflatable elements located at the distant or leading end of the catheter. One of these elements is a distal balloon that in operation of the catheter is located just beyond the vessel section to be cleared. Another element is a proximal balloon that is located just before the blood vessel section containing the plaque. The channels connected to these two balloons permit fluid pressure to selectively expand the balloons by inflation and collapse them by deflation. A third channel provides fluid under pressure to a milling balloon that rotates to cut away or mill the plaque and which may be gradually expanded. Another channel is provided to withdraw the plaque particles out of the blood vessel as they are being cut or milled away.

BRIEF DESCRIPTION OF THE DRAWINGS

The foregoing and still other objects and advantages of the present invention will be more apparent from the following detailed explanation of the preferred embodiments of the invention considered in connection with the accompanying drawings herein in which:

FIG. 2 is a cross section of the leading end of the catheter with the balloons deflated;

FIG. 3 is a view similar to FIG. 2 with the catheter inserted in a blood vessel to the section that is partially blocked by atherosclerotic plaque;

FIG. 4 is similar to FIG. 3 with the balloons located in their appropriate positions prior to inflation;

FIG. 5 illustrates the catheter in place with the distal and proximal balloons inflated sealing off the occluded vessel section and the milling balloon partially inflated and in position to cut away the atheroscloerotic plaque;

DESCRIPTION OF A PREFERRED EMBODIMENT

Figure 1:
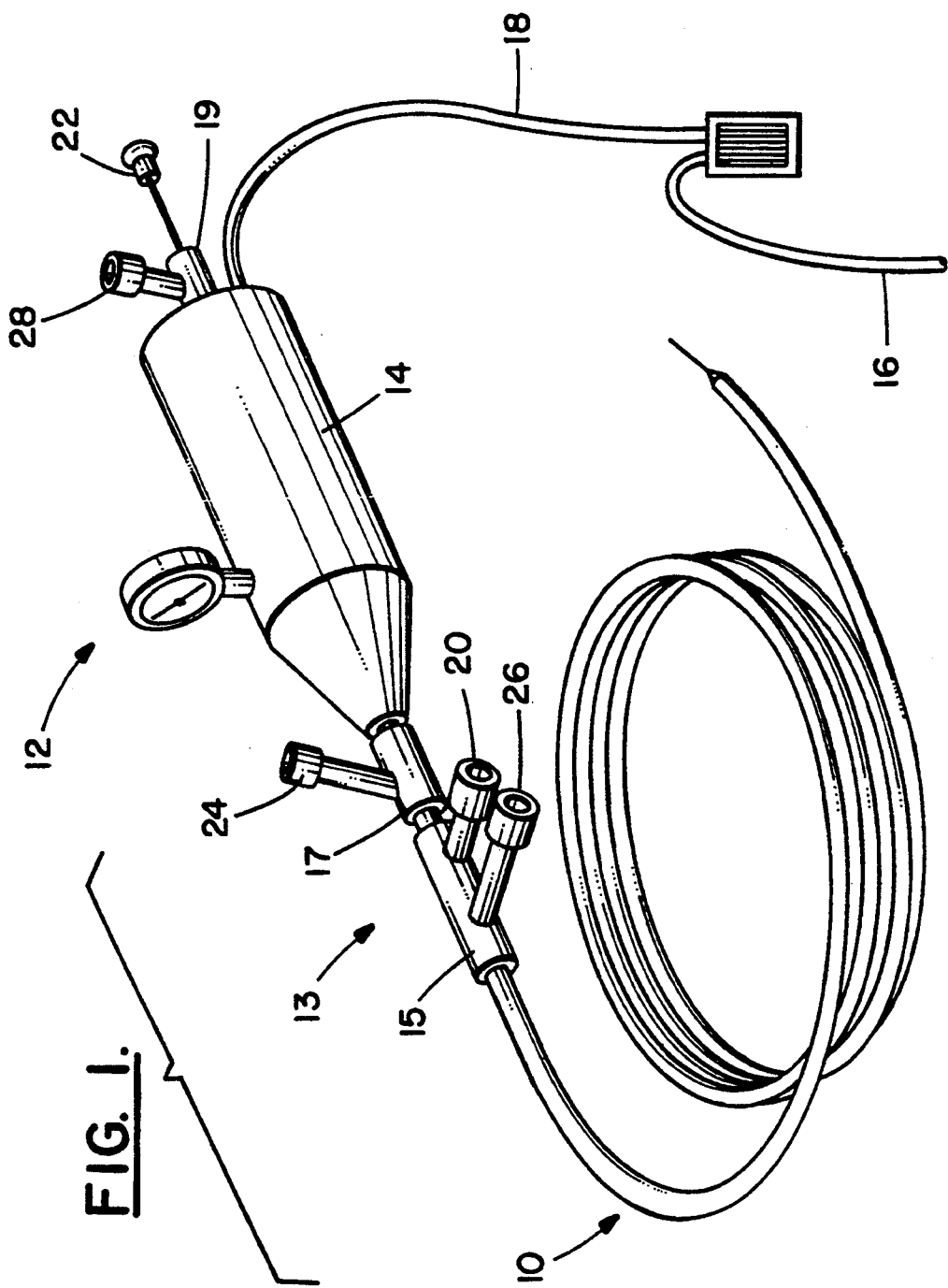
FIG. 1 is a perspective view of the apparatus of the present invention showing the catheter and control mechanism.

Referring to FIG. 1 there is shown an elongated flexible catheter 10 connected to a control mechanism 12 by suitable tubular connectors 13. The control mechanism includes a hand-held rotator 14 connected to a power source 16 through a variable speed control unit 18 which may take the form of a foot switch. The power source may be electrical, pneumatic or other means to provide power to the rotator unit 14.

The leading end of the catheter contains a number of inflatable balloons, as hereinafter described, and a number of fluid channels extending the length thereof to selectively inflate and deflate the balloons. The control mechanism 12 provides appropriate apparatus to connect and control the fluids, under pressure, in the catheter channels.

Thus the catheter has an extension pipe 15 having connectors 20, 26, pipe 17 having connector 24 and a pipe 19 having connector 28. It is understood that a source of fluid pressure is connected to each of these connectors, and selectively controlled to inflate and deflate the respective balloons. Connectors 26 and 28 provide a system for the infusion of fluid and for the withdrawal of particles of plaque as they are milled or cut away. Connector 28 permits the infusion of the flushing fluid to the area of the blood vessel being treated as explained hereinafter. The flushing fluid will pick up the particles of plaque and carry them to be expelled by the debris collection connector 26. The sources of fluid pressure connected to connectors 20, 22 and 24 are of any general type well known to the prior art and not herein shown. Similarly the source of the infusion flushing fluid connected to port 28 may take any convenient form and is similarly not herein illustrated.

Figure 6:
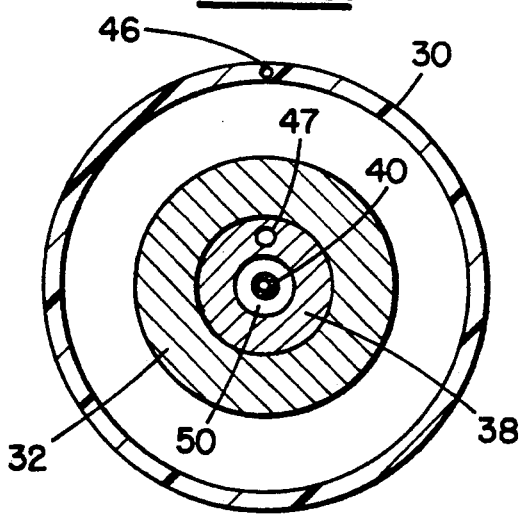
FIG. 6 is a sectional view on the line 6—6 of FIG. 2.
Figure 7:
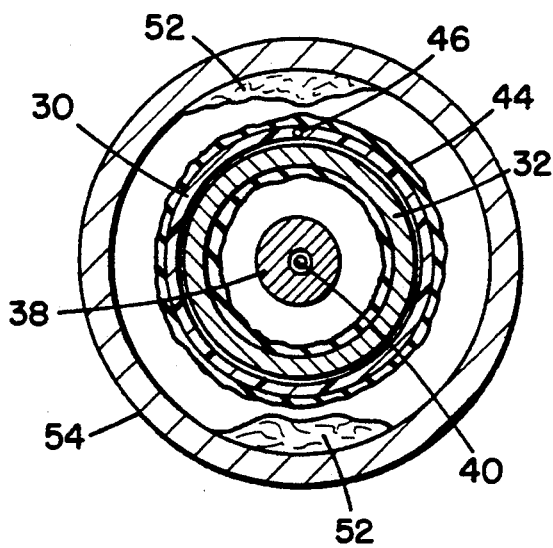
FIG. 7 is a sectional view taken on the line 7—7 of FIG. 3.
Figure 8:
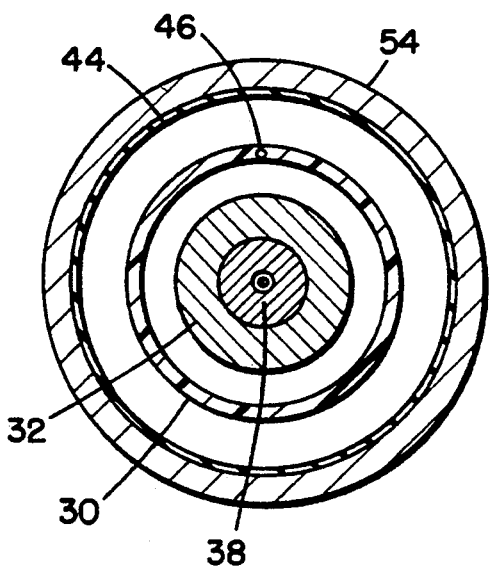
FIG. 8 is a sectional view taken on the line 8—8 of FIG. 5.
Figure 9:
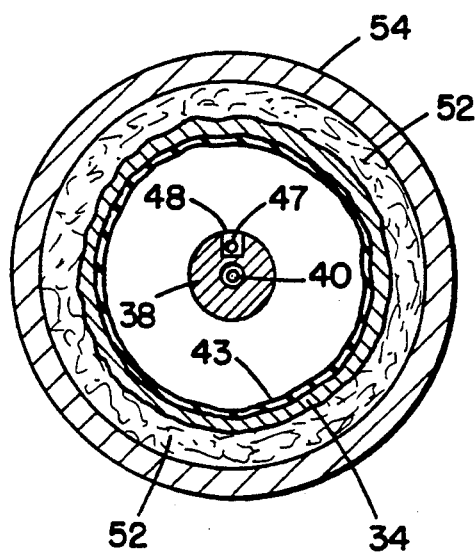
FIG. 9 is a sectional view taken on the line 9—9 of FIG. 5.

It is understood that the various elements of catheter 10 are made of flexible material so that the catheter may be inserted through a puncture in a patient's skin and passed to an area in the blood vessel wall that requires treatment. Referring now to FIGS. 2 and 6 there is shown the construction of the catheter which includes an outer sheath 30 that serves as a housing for the elements of the flexible catheter. This sheath may be made of an inert plastic material about 2 mm. in diameter. Within the sheath is a drive cable 32 adapted to be rotated as hereinafter described and containing a section 34 that is expandable under fluid pressure. The drive cable comprises a mesh of woven stainless steel wires.

The weave is somewhat loose so that the wire mesh can expand radially as hereinafter described. This type of loosely woven stainless steel wire mesh is well known and commercially available. An abrasive tip 36 is secured to the outer end of the drive cable and will rotate with it to facilitate the passage of the leading end of the catheter past the arterial deposit on the blood vessel wall at the section requiring clearing. A tube 38 is located within the drive cable and within the tube is a hollow guide wire 40 having the distal balloon 42 secured to it at its outer end.

Radial ports (not shown) are provided in the outer or leading end of hollow guide wire 40 that connect with the balloon 42 to permit its inflation by fluid passing through the hollow guide wire and the ports to the interior of the balloon.

Located on the outer surface of sheath 30 is a proximal balloon 44 which is also adapted to be inflated by fluid pressure which is directed through a channel 46 in the sheath and through a radial port connecting the channel with the proximal balloon 44. Another channel 47 extends the length of tube 38 as seen more clearly in FIG. 6 and through a radial port 48 permits fluid under pressure to expand milling balloon 43 located on the outer surface of the tube 38 and in contact with a section of the mesh drive cable. Thus as fluid under pressure passes through channel 47 and port 48 it will gradually expand milling balloon 43 which in turn causes the associated section of the rotating mesh cable to expand. This section's outer surface is roughened and will serve to mill or cut away the plaque obstruction in the blood vessel. In particular the cable section may be roughened by applying abrasive material such as zirconium particles to the outer surface with an adhesive material. Alternatively abrasive particles may be plated onto the mesh.

In order to carry away the particles that are milled from the internal wall of the vessel, an infusion channel 50 exists between the outer surface of the guide wire and the inner surface of tube 38 as seen in FIG. 6. This channel permits a flushing fluid to wash or flush away the particles which will be carried through a debris removal channel 49 existing between the tube 38 and drive cable 32.

The operation of the device would occur in the following manner. After a previously identified atherosclerotic vascular obstruction or plaque deposit 52 has been identified for treatment because its presence limits the flow of nutrient blood to vital tissues, the device would be inserted through a small skin puncture into the arterial system. Under fluoroscopic control the guide wire will lead the catheter through the blood vessel 54 to a point where the blockage occurs as shown in FIG. 3. It is seen that the leading end of the guide wire with the distal balloon attached passes through the blocked blood vessel section followed by the abrasive tip 36. The tip may be rotated to facilitate passage through the plaque section. At this point the outer sheath 30 is withdrawn and the catheter is in the condition shown in FIGS. 4 and 5. At this point, the distal balloon 42 and proximal balloon 44 are expanded or inflated by fluid pressure being applied to their respective connectors 22 and 20 shown in FIG. 1. With these balloons expanded as seen in FIG. 5, the section of blood vessel to be treated is sealed from the remaining portions of the vessel and fluid pressure is applied to connector 24 to partially expand the milling balloon 43 and at the same time the rotator 14 is rotating drive cable 32 which in turn rotates the milling section 34. As the plaque is cut away the milling balloon 43 is gradually inflated to increase its diameter as plaque is being ground off the surface of the artery. At the same time a flushing fluid is being applied to infusion converter 24 to carry away the plaque debris which is being continually flushed out through channel 49 and collection port 26. It is seen then that the milling section 34 of mesh cable 32 is gradually expanded under pressure from the expanding milling balloon 43 as the plaque is milled away from the occluded section of the blood vessel. This is a particularly advantageous feature of the present invention.

In the event drug treatment of the diseased length of vessel is desired such drugs or other therapeutic materials may be given via the infusion port 24.

When the plaque 52 in the section being treated has been milled away the balloons are deflated and the end of the catheter is withdrawn back into the outer sheath 30 and removed from the blood vessel.

Having thus described the invention with particular reference to the preferred forms thereof, it will be obvious that various changes and modifications may be made therein without departing from the spirit and scope of the invention as defined in the appended claims.

We claim:

1. An angioplasty apparatus for removing deposits of atheromatic plaque from the interior walls of blood vessels comprising:
    an elongated flexible catheter having an outer end adapted to be inserted into a blood vessel to the location of a plague deposit section of the vessel including;
    a hollow wire within the catheter extending the length thereof and providing a first channel;
    an inflatable distal balloon secured to the outer end of the guide wire and adapted to be inflated by fluid passing through the first channel;
    tube means surrounding the guide wire and extending the length of the catheter and having a second channel extending a substantial length thereof;
    a drive cable surrounding the tube means;
    a section of the drive cable being radially expandable;
    the outer surface of said drive cable section being roughened to form a milling surface;
    said second channel terminating at the said drive cable section whereby the section may be radially expandable by fluid passing through said second channel;
    sheath means surrounding the drive cable and extending the length of the catheter and having a third channel extending a substantial length thereof;
    an inflatable proximal balloon surrounding said sheath means at the outer end thereof connected to the third channel and adapted to be inflated by fluid passing therethrough;
    means connected to the drive cable to cause rotation thereof whereby the expanded section will mill the atheromatic plaque on the interior blood vessel wall producing free particles of plague;
    the space between the sheath means and drive cable providing a fourth channel to withdraw the free plague particles, and
    means to selectively supply fluid pressure to said first, second and third channels to inflate the distal balloon, expand the cable section and inflate the proximal balloon respectively.

2. The apparatus set forth in claim 1 including a fluid channel between the outer surface of the guide wire and the tube means whereby a flushing fluid may be passed to flush plague particles through the fourth channel.

3. The apparatus set forth in claim 2 including an abrading tip secured to the outer end of the drive cable adapted to be rotated to facilitate the insertion of the catheter to the plague deposit section.

4. The apparatus set forth in claim 3 in which the drive cable is axially movable within the sheath means whereby the expandable section of the drive cable is within the sheath during insertion of the catheter in the blood vessel and the sheath may be partially withdrawn to expose the expandable milling section to the plaque area of the blood vessel wall.

5. An angioplasty apparatus for removing deposits of atheromatic plaque from the interior walls of blood vessels comprising:
    an elongated flexible catheter having an outer end adapted to be inserted into a blood vessel to the location of a plague deposit section of the vessel including;
    tube means extending the length of the catheter and having a channel extending a substantial length thereof;
    a flexible drive cable surrounding the tube means;
    a section of the drive cable being radially expandable;
    the outer surface of said drive cable section being roughened to form a milling surface;
    said channel terminating at the said drive cable section whereby the section may be radially expandable by fluid under pressure passing through said channel; and
    means connected to the drive cable to cause rotation thereof whereby the expanded section will mill the atheromatic plaque on the interior blood vessel wall producing free particles of plague.

6. The apparatus set forth in claim 5 including a balloon surrounding the tube means and contacting the inner surface of the said roughened drive cable section;
    said balloon being in contact with the said channel whereby fluid pressure in the channel will expand the balloon to selectively expand the said drive cable section whereby the section may be gradually expanded as the plague deposit is milled away.

7. The apparatus set forth in claim 6 in which the said tube channel has radially ports interconnecting the channel and the said balloon.

8. An angioplasty apparatus for removing deposits of atheromatic plague from the interior walls of blood vessels comprising:
    an elongated flexible catheter having an outer end adapted to be inserted into a blood vessel to the location of a plague deposit section of the vessel including:
    a hollow wire within the catheter extending the length thereof and providing a first channel;
    an inflatable distal balloon secured to the outer end of the guide wire and adapted to be inflated by fluid under pressure in the first channel;
    tube means surrounding the guide wire and extending the length of the catheter and having a second channel extending a substantial length thereof;
    a drive cable surrounding the tube means;
    the outer surface of said drive cable having a section being roughened to form a milling surface;
    said second channel terminating at the said drive cable section whereby the section may be radially expandable by fluid passing through said second channel;

sheath means surrounding the drive cable and extending the length of the catheter and having a third channel extending a substantial length thereof;

an inflatable proximal balloon surrounding said sheath means at the outer end thereof connected to the third channel and adapted to be inflated by fluid under pressure in said third channel;

means connected to the drive cable to cause rotation thereof whereby the expanded section will mill the atheromatic plague on the interior blood vessel wall producing free particles of plaque;

means to selectively supply fluid pressure to said first, second and third channels to inflate the distal balloon, expand the cable section and inflate the proximal balloon respectively.

9. The apparatus set forth in claim 8 whereby said outer sheath, drive cable and guide wire are relatively axially movable whereby axial movement will permit the distal balloon to be located beyond a plaque deposit, the proximal balloon forward of a plaque deposit and the roughened cable section within the plaque deposit.

* * * * *